United States Patent [19]

Izawa et al.

[11] Patent Number: 5,858,952
[45] Date of Patent: Jan. 12, 1999

[54] ENZYME-CONTAINING GRANULATED PRODUCT METHOD OF PREPARATION AND COMPOSITIONS CONTAINING THE GRANULATED PRODUCT

[75] Inventors: Yoshifumi Izawa; Takaaki Watanabe; Nobuharu Kotani, all of Kashima-gun, Japan

[73] Assignee: Kao Corporation, Tokyo, Japan

[21] Appl. No.: 757,561

[22] Filed: Nov. 27, 1996

[30] Foreign Application Priority Data

Dec. 22, 1995 [JP] Japan ................................ 7-335250

[51] Int. Cl.$^6$ .............................. C11D 3/386; C11D 3/02
[52] U.S. Cl. .................... 510/392; 510/530; 510/305; 510/306; 510/320; 510/349; 510/441
[58] Field of Search ...................... 510/392, 530, 510/305, 306, 320, 349, 441

[56] References Cited

U.S. PATENT DOCUMENTS

| | | | |
|---|---|---|---|
| 4,009,076 | 2/1977 | Green et al. ................... | 195/63 |
| 4,381,247 | 4/1983 | Nakagawa et al. ............. | 252/95 |
| 4,707,287 | 11/1987 | Herdeman ...................... | 252/91 |
| 4,863,626 | 9/1989 | Coyne et al. .................. | 252/91 |
| 4,973,417 | 11/1990 | Falholt .......................... | 252/95 |
| 5,093,021 | 3/1992 | Coyne et al. .................. | 252/91 |
| 5,167,854 | 12/1992 | Deleeuw et al. ............... | 252/186.27 |
| 5,225,102 | 7/1993 | Coyne et al. .................. | 252/186.26 |
| 5,254,287 | 10/1993 | Deleeuw et al. ............... | 252/186.27 |
| 5,324,649 | 6/1994 | Arnold et al. .................. | 435/187 |
| 5,624,684 | 4/1997 | Fuisz ............................. | 424/484 |
| 5,721,205 | 2/1998 | Barnabas et al. .           | |

FOREIGN PATENT DOCUMENTS

| | | |
|---|---|---|
| 0206418 | 12/1986 | European Pat. Off. . |
| 0360323 | 3/1990 | European Pat. Off. . |
| 0381262 | 8/1990 | European Pat. Off. . |

OTHER PUBLICATIONS

English language abstract of JP2135070.
English language abstract of JP62210988.

*Primary Examiner*—Kery A. Fries
*Attorney, Agent, or Firm*—Birch, Stewart, Kolasch & Birch, LLP

[57] ABSTRACT

The present invention provides an enzyme-containing granulated product containing, in a uniformly dispersed state, an enzyme and one or more stabilizers selected from the group consisting of reducing agents and antioxidants. The invention also discloses a method for the production of the granulated product, as well as bleaching agents and detergent compositions containing the granulated product. The granulated product loses only a minimal level of enzyme activity even in the copresence of a bleaching agent, and exhibits excellent solubility. Therefore, bleach compositions and detergent compositions prepared by incorporating the granulated product fully exhibit the enzyme activity and bleaching activity.

16 Claims, No Drawings

ENZYME-CONTAINING GRANULATED PRODUCT METHOD OF PREPARATION AND COMPOSITIONS CONTAINING THE GRANULATED PRODUCT

BACKGROUND OF THE INVENTION

1. Field of the Invention

The present invention relates to an enzyme-containing granulated product having improved stability, and more particularly to an enzyme-containing granulated product that undergoes only minimal reduction in activity even in the presence of peroxides typified by bleaching agents. The invention also relates to methods for preparing such products as well as to bleach compositions and detergent compositions containing the product.

2. Description of the Related Art

Detergents and bleaches for clothing frequently contain a variety of enzymes, in addition to surfactants or bleaching ingredients, in an effort to improve detergent power. These enzymes are usually incorporated in the form of granules so as not to lose their activity during storage and to sufficiently exhibit their activities during washing. The enzymatic stability of such enzyme-containing granulated products decreases when the granulated products are blended with bleaching agents, surfactants, builders for detergents, or similar materials. In particular, it is known that enzyme activity decreases considerably when a granulated product is blended with a bleaching agent.

Measures to prevent the reduction of enzyme activity of enzyme-containing granulated products are disclosed by Japanese Patent Application Laid-Open (kokai) No. 62-79298, which describes an enzyme composition in which the core part containing an enzyme is coated with a protective layer containing an alkaline buffering salt of pH 7–11, and by Japanese Patent Application Laid-Open (kokai) No. 3-149298, which describes a bleaching agent containing hydrase particles, in which the enzyme nuclei are coated with a protective agent such as a water-soluble alkali metal silicate, a transition metal, or a reducing agent.

However, those conventional methods for stabilizing enzymes have a problem in that when the thickness of the coating layer is increased or a large amount of a water-soluble substance is incorporated into the coatings so as to fully stabilize the enzymes, the enzyme-containing granulated products come to have reduced solubility in water, and therefore the detergent power of enzymes cannot be sufficiently exerted during use in washing. On the other hand, when the thickness of the coating layer is reduced for the purpose of solubility, the enzymes cannot be satisfactorily stabilized.

Under the above circumstances, the present inventors conducted a variety of studies regarding means for stabilizing enzymes, and found that, so far as enzymes, such as hydrolase, are concerned, the copresence, in a uniformly dispersed state, of such an enzyme, and a stabilizing agent, such as a reducing agent or an antioxidant, is effective in avoiding deactivation of the enzyme and provides a granulated product having excellent solubility. This is surprising because in the past, it has been customary in the preparation of such a granulated product to separate an enzyme from a reducing agent by the use of a coating or the like. The present invention was accomplished based on this finding.

SUMMARY OF THE INVENTION

Accordingly, the present invention provides an enzyme-containing granulated product comprising an enzyme and one or more stabilizers selected from the group consisting of reducing agents and antioxidants; and a method for preparing such a product.

The present invention also provides a bleach composition comprising the enzyme-containing granulated product and a bleaching agent.

The present invention also provides a detergent composition comprising the enzyme-containing granulated product and a surfactant.

DETAILED DESCRIPTION OF PREFERRED EMBODIMENTS

The enzyme-containing granulated product of the present invention comprises, in a uniformly dispersed state, an enzyme, and one or more stabilizers selected from the group consisting of reducing agents and antioxidants. As used herein, the expression "in a uniformly dispersed state" refers to a state in which an enzyme and stabilizer are not segregated in separate layers, and therefore, an enzyme and a stabilizer are not necessarily in a dispersed state on the molecular level and they may be present as a dispersed powder.

Enzymes which are used in the present invention are not particularly limited so long as they can be incorporated into bleaching agents or detergents. Preferably, hydrolases are used, and specifically, proteases, esterases, and carbohydrases are used.

Specific examples of proteases include pepsin, trypsin, chymotrypsin, collagenase, keratinase, elastase, subtilisin, papain, aminopeptidase, and carboxypeptidase.

Specific examples of esterases include gastric lipase, pancreatic lipase, lipases of vegetable origin, phospholipases, choline esterases, and phosphatases.

Specific examples of carbohydrases include cellulase, maltase, saccharase, amylase, pectitase, and $\alpha$- and $\beta$-glycosidases.

The stabilizer used in the present invention is a reducing agent, an antioxidant, or a mixture of two or more of reducing agents or antioxidants. Reducing agents and antioxidants are preferably used in combination.

Examples of reducing agents include alkali metal salts (such as sodium salts and potassium salts) and alkaline earth metal salts (such as calcium salts and magnesium salts) of boric acid, sulfurous acid, thiosulfuric acid, etc. Specifically, sodium tetraborate, sodium sulfite, and sodium thiosulfate are used. Specific examples of antioxidants include ascorbic acid, sodium ascorbate, erythorbic acid, sodium erythorbate, dl-$\alpha$-tocopherol, isopropyl citrate, butylated hydroxytoluene (BHT), butylated hydroxyanisol (BHA), tannic acid, and sulfur-containing antioxidants. Of these, sodium tetraborate, sodium erysorbate, and mixtures thereof are particularly preferred.

The enzymes and stabilizers may be used singly or in combinations of two or more. The amount of enzymes contained in the granulated product is not particularly limited. In consideration of the effect desired when the enzymes are incorporated into detergents or bleaching agents, it is generally preferred that the amount of the enzymes be between 0.01 and 50% by weight, and more preferably between 0.1 and 30% by weight. The amount of stabilizers vary depending on the types of enzymes employed. It is preferred that the stabilizers be incorporated at a concentration between 0.1 and 3,000% by weight, more preferably between 1 and 500% by weight, and particularly preferably between 10 and 300% by weight, calculated in relation to the amounts of enzyme protein. When a reducing agent and an antioxidant are used in combination, the ratio (by weight) of the reducing agent to the antioxidant which are to be incorporated is between 1/9 and 9/1, preferably between 1/3 and 3/1, and particularly preferably between 1/3 and 1/1.

The granulated product of the present invention may contain further additives, in addition to the above-mentioned components, which are needed for granulation. Such additives include binders, particularly water-soluble organic binders. The following may be cited as examples of water-soluble organic binders that can be used together with the mentioned essential components of the present invention: (a) water-soluble polymers selected from the group consisting of polyethylene glycol having a melting point of not lower than 35° C., derivatives thereof, and polyoxyethylene polyoxypropylene copolymers; (b) nonionic surfactants having a melting point or pour point of not lower than 35° C.; and (c) polycarboxylates having a mean molecular weight of not less than 4,000. These may be used singly, or in combinations of two or more.

Specific examples of particularly preferred water-soluble organic binders include, among the class of polyethylene glycol and its derivatives (a), polyethylene glycol, polyethylene glycol sulfate, and methoxypolyethylene glycol; among the class of nonionic surfactants (b), polyoxyethylene alkyl ethers; and among the class of polycarboxylates (c), alkali metal salts of polyacrylic acid, acrylic acid/maleic acid copolymers, and polyacetal carboxylate.

These water-soluble organic binders are advantageous, since they are components which are also used in detergent compositions. The amount of usually-employed water-soluble organic binders is not univocally determined, as their properties vary from binder to binder. However, under general circumstances, those which exhibit binding power at a minimum concentration are usually preferred as they provide room for maximizing the enzyme activity of the resultant enzyme-containing granulated products. From this point, these water-soluble organic binders are usually incorporated in an enzyme-containing granulated product at a concentration of 5 to 50% by weight, and preferably 10 to 30% by weight.

According to the present invention, powdery bulking agents may also be added if needed. Exemplary bulking agents include one or more inorganic salts selected from the group consisting of sulfates, carbonates, and hydrochlorides of alkali metals or alkaline earth metals. Of these, water-soluble inorganic alkali metal salts such as sodium sulfate, sodium carbonate, and sodium chloride are particularly preferred in view that they do not adversely affect detergent power. Other useful bulking agents include water-soluble organic salts such as sodium citrate; talc, titanium oxide, calcium carbonate, zeolite, magnesium carbonate, activated clay, and kaolin.

The granulated product of the present invention may also contain a variety of inorganic salts such as calcium salts and magnesium salts; as well as organic materials including surfactants, saccharides, and carboxymethylcellulose. Moreover, if synthesized hectorite or sepiolite is incorporated, odoriferous components derived from cultivation can be adsorbed. The enzyme-containing granules may be colored by incorporating thereto colorants or dyes.

The method for the manufacture of the granulated product of the present invention is not particularly limited so long as it is capable of incorporating an enzyme and a stabilizer in a uniformly dispersed state. For example, any of the following methods may be used: (1) a solution containing an enzyme and a stabilizer is dried, followed by granulation; (2) a solution containing an enzyme and a stabilizer is subjected to a wet granulation process; and (3) an enzyme powder and a stabilizer powder are uniformly blended, followed by granulation. Of these, method (1) is particularly preferred.

In method (1) above, the solution containing an enzyme and a stabilizer is preferably an aqueous solution, and more preferably an aqueous solution containing a buffer agent. The solution may be dried via spray-drying, freeze-drying, etc., with spray-drying being particularly preferred. Means for granulating the resultant dry powder is not particularly limited, and wet granulation and dry granulation are both preferable. Illustrative granulation methods include extruding, tumbling, fluidized-bed granulation, spray granulation, and disintegration granulation. Among them, tumbling granulation, particularly tumbling granulation with agitating blades, is preferred. Examples of mixing tumbling granulation machines are a Henschel mixer (Mitsui-Miike Kakoki K. K.), a high-speed mixer (Fukae Kogyo K. K.), and a vertical granulator (Fuji Sangyo K. K.). These three share a common feature of having a vertical agitator axis with a mixing blade inside a mixing tank of a vertical type. A granulator having a horizontal agitator axis, a Loedige mixer (Loedige Co.), may also be used.

When method (2) is used, a solution containing an enzyme and a stabilizer can be prepared in a manner similar to that of method (1).

In method (3), dry-format granulation is performed.

The particle size of the thus-obtained granulated product is not particularly limited. The mean particle size is generally between 200 and 3,000 $\mu$m, and preferably between 350 and 1,500 $\mu$m.

The enzyme-containing granulated product of the present invention preferably has a coating thereon so as to obtain even further improved stability, though the product may be used without coating.

Materials used for coating the enzyme-containing granulated product of the present invention are not particularly limited. They may be water-soluble film-forming polymers such as polyethylene glycol, polyacrylate, polyvinyl alcohol, polyvinyl pyrrolidone, cellulose derivatives, and starch derivatives; combinations of these polymers and water-soluble or slightly-soluble inorganic particles such as talc, clay, titanium oxide, calcium carbonate, etc; or combinations of the polymers and protective agents such as alkali metal silicate and alkali metal carbonates.

Coating materials are preferably used in a ratio by weight of 0.1 to 0.7, particularly preferably 0.2 to 0.6, when the amount of the enzyme-containing granulated product is taken as 1.

The enzyme-containing granulated product of the present invention may be coated through a conventional method using a fluidized bed granulator, a granulator equipped with a coating pan, or a mixing granulator.

Since the granulated product of the present invention is very stable against a variety of peroxides which are used as bleaching agents, when the granulated product and a bleaching agent are blended it is possible to obtain a bleaching agent exhibiting stable enzyme activity and providing an excellent bleaching effect. Examples of useful bleaching agents include sodium percarbonate, sodium perborate, sodium hypochlorite, and dichloroisocyalic acid. They are usually incorporated in bleaching compositions at a concentration of 10 to 95%, preferably 50 to 80%.

The granulated product of the present invention maintains excellent enzyme stability even when it is formed into a detergent composition containing a bleaching agent and a surfactant. Bleaching agents which are useful in this case are the same as those listed above. The amount of bleaching agents is 0.5–45% by weight, and particularly preferably 1–20% by weight.

The amount of the enzyme-containing granulated product to be incorporated into a detergent composition varies depending on the specific activity in the enzyme powder, type of the enzyme, content of the enzyme in the granulated product, etc. It is preferably between 0.001 and 70% by weight, and particularly between 0.1 and 10% by weight.

The following may be mentioned as examples of surfactants which are used in the present invention: anionic surfactants, e.g., alkylbenzene sulfonates, alkyl or alkenyl ether sulfates, alkyl or alkenyl sulfates, olefin sulfonates, alkane sulfonates, saturated or unsaturated fatty acid salts, alkyl or alkenyl ether carboxylates, a-sulfofatty acid salts or esters, amino acid-type surfactants, N-acylamino acid-type surfactants, alkyl or alkenyl acid phosphates, alkyl or alkenyl phosphates, and their salts; amphoteric surfactants, e.g., carboxy or sulfobetaine-type surfactants; nonionic surfactants, e.g., polyoxyalkylene alkyl or alkenyl ethers, polyoxyethylene alkylphenyl ethers, higher fatty acid alkanolamides and their alkylene oxide adducts, sucrose fatty acid esters, fatty acid glycerol monoesters, alkyl amine oxides, and alkyl glycosides; and cationic surfactants, e.g., quaternary ammonium salts. These surfactants are preferably incorporated in the detergent composition of the present invention at a concentration of 10–90% by weight, and particularly preferably 10–50% by weight.

Preferably, the detergent composition of the present invention contains inorganic electrolytes and chelating agents. Examples of inorganic electrolytes include carbonates, hydrogen carbonates, silicates, borates, and alkanolamines and sulfates. They are usually incorporated in amounts between 0 and 90% by weight, and preferably between 1 and 40% by weight.

Examples of chelating agents include phosphates such as tripolyphosphates, pyrophosphates, and orthophosphates; salts of phosphonic acid such as ethane-1,1-diphosphonic acid; salts of phosphonocarboxylic acid such as 2-phosphonobutanel, 2-dicarboxylic acid; salts of amino acids such as aspartic acid and glutamic acid; aminopolyacetates such as nitrilotriacetate and ethylenediaminetetraacetate; polymer chelating agents such as polyacrylic acid and polyaconitic acid; salts of organic acids such as oxalic acid and citric acids; and aluminosilicates. These chelating agents are usually incorporated in a detergent composition at a concentration of between 0 and 50% by weight, with between 1 and 30% by weight being more preferred.

Optional ingredients may be incorporated as desired in small amounts. Such optional ingredients include anti-redeposition agents, e.g., polyethylene glycol and carboxymethylcellulose; fluorescent dyes; bluing agents; colorants; caking preventive agents; solubilizers; enzymes or activators for bleaching agents; and metal corrosion inhibitors.

The detergent composition of the present invention can be prepared by blending the above-mentioned ingredients to thereby form a granular detergent composition for clothing, dishes, and for house cleaning, according to conventional methods.

EXAMPLES

The present invention is further illustrated by the following Examples, which should not construed as limiting the invention.

Example 1

(1) An aqueous solution containing a crude enzyme having an amylase activity (derived from *Bacillus sp.* KSM-AP1378 (FERM BP-3048) was used as an aqueous enzyme solution (concentration of enzyme protein: 0.3% by weight). To this solution, sodium tetraborate (indicated as A in Table 1) and sodium erythorbate (indicated as B in Table 1) were added as stabilizers so that the amount of the stabilizers became 1–10 times that of the mass of the enzyme protein in the aqueous solution (on a weight basis). The thus-prepared mixtures were used as samples.

(2) A control sample (which did not contain a stabilizer) and the sample prepared in (1) were spray-dried by the application of 150° C. air produced by an atomizer-type spray drier (temperature of exhaust air: 75° C.), thereby obtaining a solid granular enzyme preparation.

(3) The stability of the enzyme in a bleaching agent was assessed by measuring the percentage residual activity after storage at 40° C. and a relative humidity of 80% for 3 days. As a model bleaching agent, a composition including 85% by weight of sodium percarbonate, 3% by weight of linear alkyl($C_{12}$–$C_{13}$)benzenesulfonate, and 12% by weight of sodium carbonate was used. This bleaching composition was blended with the solid granular enzyme preparation at a ratio of 5:1 (by weight) and the resultant mixture was stored under the above-mentioned conditions. the results are shown in Table 1.

TABLE 1

| Samples (stabilizer, enzyme protein:stabilizer (ratio by weight)) | Residual activity (%) |
|---|---|
| Control | 5 |
| Sample 1 (A, 1:1.5) | 10 |
| Sample 2 (A, 1:5) | 25 |
| Sample 3 (A, 1:10) | 30 |
| Sample 4 (B, 1:2.5) | 20 |
| Sample 5 (B, 1:5) | 25 |
| Sample 6 (A, 1:5 B, 1:2.5) | 57 |
| Sample 7 (A, 1:10 B, 1:2.5) | 74 |

Example 2

An enzyme-containing granulated product prepared in Example 1 and, for comparison, a granulated product coated by the addition of a stabilizer during the step of granulation were incorporated into a bleaching agent. The general procedure of Example 1 was repeated, and the stability of the enzyme was assessed by measuring the percentage residual activity after storage at 40° C. and a relative humidity of 80% for 5 days. The results are shown in Table 2. In Table 2, Comparative Sample 1 was prepared by coating a granulated product which was identical to the control product using a stabilizer in the amount same as that employed in the preparation of Sample 7. Sample 7 was the same as that used in Example 1.

TABLE 2

| Samples | Residual activity (%) |
|---|---|
| Control (without a stabilizer) | 5 |
| Comparative Sample 1 (coated with a stabilizer) | 6 |
| Sample 7 (same as that used in Example 1) | 80 |

Example 3

An aqueous solution of a crude enzyme having cellulase activity (derived from *Bacillus sp.* KSM635-KNV (FERM P-13549)) was used as an aqueous enzyme solution (concentration of enzyme protein: 2.5% by weight). To this solution, sodium tetraborate (indicated as A in Table 3) and sodium erythorbate (indicated as B in Table 3) were added as stabilizers so that the amount of the stabilizers became 1–2 times that of the mass of the enzyme protein in the aqueous solution (on a weight basis). The thus-prepared mixtures were used as samples. Subsequently, a similar procedure as described in Example 1 was performed.

TABLE 3

| Samples (stabilizer, enzyme protein:stabilizer (ratio by weight)) | Residual activity (%) |
| --- | --- |
| Control | 16 |
| Sample 8 (A, 1:1 B, 1:1) | 91 |
| Sample 9 (A, 1:2 B, 1:2) | 98 |

Example 4

An aqueous solution of a crude enzyme having protease activity (derived from *Bacillus sp.* KSM-K16 (FERM P-3367)) was used as an aqueous enzyme solution (concentration of enzyme protein: 7.5% by weight). To this solution, sodium tetraborate (indicated as A in Table 4) and sodium erythorbate (indicated as B in Table 4) were added as stabilizers so that the amount of the stabilizers became 0.25 to 0.5 times that of the mass of the enzyme protein in the aqueous solution (on a weight basis). The thus-prepared mixtures were used as samples. Subsequently, a similar procedure as described in Example 1 was performed.

TABLE 4

| Samples (stabilizer, enzyme protein:stabilizer (ratio by weight)) | Residual activity (%) |
| --- | --- |
| Control | 11 |
| Sample 10 (A, 1:0.25 B, 1:0.25) | 76 |
| Sample 11 (A, 1:0.5 B, 1:0.5) | 77 |

Example 5

The control sample and Sample 6 prepared in Example 1 were coated as described below, and the stability, in a bleaching agent, of the enzyme contained in the resultant coated granules was assessed by measuring the percentage residual activity after storage at 40° C. and a relative humidity of 80% for 14 days. The bleaching agent was the same as the model described in Example 1. The results are shown in Table 5.

(Coating Method)

Using a mixing tumbling granulator, 66 parts by weight of each enzyme-containing granulated product was blended with 27 parts by weight of talc (mean particle size: 36 $\mu$m) and 7 parts by weight of polyethylene glycol (mean molecular weight: 6,000), all at once. Coated granules having a diameter ranging from 350 to 1,000 $\mu$m were obtained.

TABLE 5

| Samples (stabilizer, enzyme protein:stabilizer (ratio by weight)) | Residual activity (%) |
| --- | --- |
| Control (Coated with the control in Example 1) | 0 |
| Sample 12 (A, 1:5 B, 1:2.5) (Coated with Sample 6 in Example 1) | 50 |

Example 6 (Formulation of a detergent)

| Ingredients | amounts (parts by weight) |
| --- | --- |
| Sodium linear ($C_{12}$–$C_{13}$) benzenesulfonate | 10 |
| Polyoxyethylene (EO = 10) alkyl($C_{12}$–$C_{13}$) ether | 10 |
| Zeolite | 30 |
| Sodium carbonate | 10 |
| Sodium perborate | 25 |
| Enzyme-containing granulated product prepared in Example 1 | 10 |
| Water | 15 |

As described above, the granulated product according to the present invention loses only a minimal level of enzyme activity even in the copresence of a bleaching agent, and exhibits excellent solubility. Therefore, bleach compositions and detergent compositions prepared by incorporating the granulated product fully exhibit the enzyme activity and bleaching activity.

What is claimed is:

1. An enzyme-containing granulated product comprising, an enzyme and a stabilizer which comprises a mixture of reducing agents and antioxidants, wherein said enzyme is uniformly dispersed throughout said stabilizer.

2. The enzyme-containing granulated product according to claim 1, wherein the enzyme is a hydrolase.

3. The enzyme-containing granulated product according to claim 1 or 2, wherein the antioxidant is sodium tetraborate and/or sodium erythorbate.

4. The enzyme-containing granulated product according to claim 1 or 2, wherein the stabilizer is incorporated at a concentration of 0.1 to 3,000% by weight calculated in relation to the mass of enzyme protein.

5. The enzyme-containing granulated product according to claim 1 or 2, further comprising a coating.

6. A method for the manufacture of the enzyme-containing granulated product as set forth in claim 1 or 2, comprising the steps of drying a solution containing said enzyme and said stabilizer and subjecting the dry material to granulation.

7. The method according to claim 5, comprising the steps of drying a solution containing said enzyme and said stabilizer, subjecting the dry material to granulation, and coating the surfaces of the resultant granules.

8. The method according to claim 1 or 2, wherein said solution containing said enzyme and said stabilizer is wet-granulated.

9. The method according to claim 5, wherein said solution containing said enzyme and said stabilizer is wet-granulated, and subsequently coated with a coating agent.

10. The method according to claim 6, comprising uniformly mixing powder of an enzyme and powder of a stabilizer, and subsequently granulating said mixture.

11. The method according to claim 7, comprising uniformly mixing powder of an enzyme and powder of a stabilizer, granulating said mixture, and coating the surfaces of the resultant granules with a coating agent.

12. A bleaching composition comprising the enzyme-containing granulated product as described in claim 1 or 2, and a bleaching agent.

13. A detergent composition comprising the enzyme-containing granulated product as described in claim 1 or 2, a bleaching agent, and a surfactant.

14. The enzyme-containing granulated product according to claim 3, wherein the stabilizer is incorporated at a concentration of 0.1 to 3,000% by weight calculated in relation to the mass of enzyme protein.

15. A bleaching composition comprising the enzyme-containing granulated product as described in claim 5, and a bleaching agent.

16. A detergent composition comprising the enzyme-containing granulated product as described in claim 5, a bleaching agent, and a surfactant.

* * * * *